United States Patent [19]

Legrand et al.

[11] 4,383,907

[45] May 17, 1983

[54] GAS-ANALYSIS PROBE

[75] Inventors: Jacques Legrand; Jean C. Rouffy, both of Suresnes, France

[73] Assignee: Socapex, Suresnes, France

[21] Appl. No.: 285,523

[22] Filed: Jul. 21, 1981
(Under 37 CFR 1.47)

[30] Foreign Application Priority Data

Jul. 22, 1980 [FR] France ............................... 80 16122

[51] Int. Cl.³ ........................................... G01N 27/58
[52] U.S. Cl. .................................................. 204/426
[58] Field of Search .............. 204/195 S, 1 S; 338/34; 123/489; 60/276

[56] References Cited

FOREIGN PATENT DOCUMENTS 2350598 12/1977 France ............................. 204/195 S Primary Examiner—G. L. Kaplan
Attorney, Agent, or Firm—Cushman, Darby & Cushman

[57] ABSTRACT

A gas-analysis probe is provided, the sensor of which is formed by a concentration pile.

The electric signal supplied by the sensor is picked up by means of at least two metal rods which are brazed to the sensor by thermocompression on thin filler-metal layers. The connecting lead-outs are isolated in pure-alumina sheaths maintained in place in a ceramic body by a hardened liquid ceramic filling. A spring absorbs the differences in expansion and fins on the metal casing remove the heat. A perforated cap protects the sensor.

10 Claims, 6 Drawing Figures

GAS-ANALYSIS PROBE

BACKGROUND OF THE INVENTION

The invention relates to a probe for analysing the exhaust gases of an internal combustion engine and more particularly to the mechanical structure of such a probe, with a view to ensuring at one and the same time its easy industrial production, its proper operation in use and its reliability in time.

Probes for analysing the exhaust gases of internal combustion engines have as principal function the measurement of the oxygen concentration in these gases, so as to react through a computer on the petrol ratio in the air, at the intake, so as to improve the efficiency of the engine and reduce the unburnt gases at the exhaust.

More generally, this type of gas analysis probe is used for measuring the concentration of a chemical kind in a mixture, but their principal application in the form contemplated is for checking the combustion in engines.

Very generally, gas analysis probes use, for measuring the oxygen concentration, a sensor formed by a concentration pile which delivers, between its output terminals, a voltage according to Nernst's law. The conditions of use, in a turbulent and hot gas flow, compel the use of only solid components, and these concentration piles are often formed by a measuring electrode, made from platinum, which serves also as catalytic pot, a reference electrode made from nickel, and a material sensitive to oxygen such as a zirconium oxide $ZrO_2$ or titanium oxide $TiO_2$, the oxygen reference being provided by the air.

In practice, the concentration pile is in the form of a hollow ceramic body obtained by sintering zirconium oxide, having an outer face exposed to the exhaust gases and an inner face exposed to pure air. Platinum metalizations on the outer face and nickel metalizations on the inner face are deposited by any method conforming to the rules of the art, deposition by brush, by silk-screen printing or chemically. The production of a probe in this form presents a certain number of difficulties and disadvantages which are more especially:

sealing difficulties at the mounting portion of the cone in the metal body which serves for fixing it to the engine, the seal being however obligatory so as to maintain a stable pure-air reference;

poisoning of the platinum film deposited on the outer surface of the cone, by the lead which is present in the petrol. It follows that such oxygen-measuring probes are in practice not usable outside the States in which petrol is sold without lead;

the dimensions of the ceramic cone result, during start-up of the engine, in overheating thereof which is transmitted relatively slowly through the ceramic body, which is relatively insulating, and there follows a thermal shock which may cause, either damage to the ceramic body, so to the concentration pile, or leaks which accordingly falsify the pure-air reference, this latter being then polluted by exhaust gases.

SUMMARY OF THE INVENTION

The analysis probe of the invention is specially designed to use a sensor formed by thin-layer deposits on a ceramic wafer, which resolves—as will be shown subsequently—the sealing problem as well as that of poisoning of the platinum and that of resistance to thermal shocks.

This type of sensor, which is outside the field of the invention, has been described by the Applicant company, more especially in French Pat. No. 76.13 843. Its design on an alumina or ceramic wafer allows it to be placed as a whole in an exhaust-gas atmosphere, the reference being internal to the sensor, which overcomes the problems of sealing the reference with respect to the air, and the technology used, by miniaturization of the sensor, eliminates thermal shocks and allows electrical contacts to be made directly on the sensor by soldering or brazing.

Thus, the invention consists more precisely of a gas-analysis probe, comprising a miniaturized sensor 21, formed as a wafer 1 by thin-layer deposits, comprising at least two electrodes 3 and 4 and being entirely immersed in the gases to be analyzed, this probe being characterized in that it comprises:

at least two metal rods 22 and 23, brazed at one of their ends to sensor 21 and encased by means of two high-resistivity ceramic tubes 24 and 25, in which they are secured by partial crushing 26 and 27 at each end of the tube, so as to take off the electric signal;

a hollow ceramic body 28 one end of which is provided with apertures 29 and 30 of the same diameter as the outer diameter of the ceramic sheaths 24 and 25, for positioning the metal rods 22 and 23;

a filling, formed from a hardenable ceramic liquid 31, for ceramic body 28, so as to fix metal rods 22 and 23 in position;

a metal casing 33 having cooling fins 35;

a spring 37, which bears at 36 on a shoulder on the ceramic body 28 and at 38 on the metal casing 33, for absorbing the differences in expansion between the ceramic parts and the metal parts of the probe.

In a preferred embodiment, the composition of the ceramic tubes 24 and 25 contains between 99.5% and 99.7% by weight of alumina. In fact, the sensor 21 of the gas probe is formed by a pile supplying a voltage depending on the difference in oxygen concentration between these two electrodes. The concentration of oxygen contained in the gas is determined by comparison with a fixed oxygen concentration. One of the electrodes of the pile completes the combustion of the engine and absorbs the oxygen from the gas whereas the other contains a known oxygen concentration, serving as a reference. This reference electrode is an oxidized metal-metal mixture. Any current passing through the pile would modify the oxygen concentration of the reference electrode. So, the voltage is taken at the output terminals of the pile, preventing sensor 21 from delivering a current. The ceramic tubes 24 and 25 made from alumina of a purity between 99.5% and 99.7% have a high resistivity. This is, at 20° C., of the order of size of $10^{14}$ $\Omega$cm, at 500° C. about $1.5.10^{11}$ $\Omega$cm and at 1000° C. about $5.10^6$ $\Omega$cm. The most current ceramics such as the ceramic of body 28 which contains for example 95% by weight of alumina have resistivities, at 20° C., of the order of size of $10^{11}$ $\Omega$cm and at 600° C. of the order of $10^7$ $\Omega$cm. The electric resistance obtained with the ceramic tubes 24 and 25 prevents electric currents from being established inside body 28 between the two metal rods 22 and 23, at temperatures less than 1000° C. The temperatures of the gases at the outlet of the engine, i.e. the working temperatures of the probe, are between 400° C. and 900° C. The ceramic tubes 24 and 25 are preferably of a thickness of about 0.5 mm. The electric resistance obtained with ceramic tubes 24 and 25 is then greater than 1 giga-ohm at 850° C.

In another preferred embodiment, a fraction 46 and 47 of both ceramic tubes 24 and 25 extends beyond apertures 29 and 30 of the ceramic body 28. The metal rods 22 and 23 extend as far as the ends of the ceramic tubes 24 and 25 and hold the sensor 21 in place beyond their exit from the ceramic tubes 24 and 25. The fractions 46 and 47 are placed within the gas flow. The fractions 46 and 47 have a length of about 2 cm. The portion of metal rod 22 introduced into the fraction 46 of ceramic tube 24 is then separated from the portion of metal rod 23 introduced into the fraction 47 of the ceramic tube 25 by the ceramic tube 24, the air, then ceramic tube 25.

The fractions 46 and 47 of ceramic tubes 24 and 25 allow the surface leak currents to be reduced. When the probe is immersed in the gases to be analysed, a quantity of particles is deposited on all the outer surfaces of the probe. This dust forms then a light layer which is more electrically conducting than the ceramics. Therefore, an electric current may be established between the ends of the metal rods 22 and 23 brazed to sensor 21. This current will be propagated along said dust layer. The fractions 46 and 47 of the ceramic tubes 24 and 25 extend the path of the surface leak currents since these latter must follow the outer surface of fraction 46 from the end of rod 22 carrying sensor 21 to the surface 32, no current being able to flow through the ceramic tube 24, then spread along surface 32 before passing along the outer surface of fraction 47 as far as the end of rod 23, carrying sensor 21. The path to be followed by the leak currents is thus multiplied by a factor 10 and the resistance provided between said ends is greater than a giga-ohm.

BRIEF DESCRIPTION OF THE DRAWINGS

The invention will be better understood from the following description which gives an industrial embodiment of an exhaust-gas sensor for motor vehicles, and refers to the accompanying figures which represent.

DESCRIPTION OF THE PREFERRED EMBODIMENTS

Figure 1:
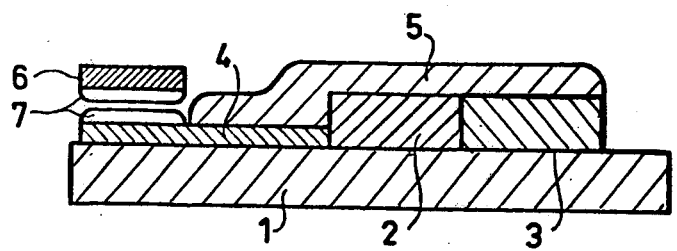
FIG. 1, a simplified diagram of a sensor mounted in the probe of the invention.

FIG. 1 shows, seen in section, the diagram of a sensor usable in the analysis probe of the invention. This sensor is outside the field of the invention and has been the subject of patent applications, but the explanation of its operation will allow the construction of the probe of the invention to be more readily understood.

On an alumina wafer 1 are deposited a zirconium oxide electrolyte layer 2 and two electrodes, one measuring electrode 3 made from platinum and a reference electrode 4 made from nickel. The platinum is deposited in a relatively thick layer permeable to the gas, in contrast to the nickel layer which is thin and impermeable. So as to prevent the zirconium oxide electrolyte from being in contact with the exhausts gases other than through the platinum measuring electrode, the whole is covered with an enamel coating 5. The reference is then a reference internal to the pile at the interface between the nickel and the zirconium oxide. The electrical contacts are taken at both ends of the wafer through steel strips or wires 6 gold-coated on the surface and soldered to a gold film deposited by silk-screen printing. The gold film 7 on the contact strip 6 and the gold film 7 deposited on the sensor are then welded together by thermocompression.

In FIG. 1, a single contact has been shown on the nickel electrode 4 side, so as to show that the platinum layer 3 has a face which is free with respect to the exhaust gases. In fact, a contact identical to that which is taken from the nickel electrode is also taken from the platinum electrode, but it will be admitted for the convenience of the drawing that this contact is hidden behind the platinum electrode.

Figure 2:
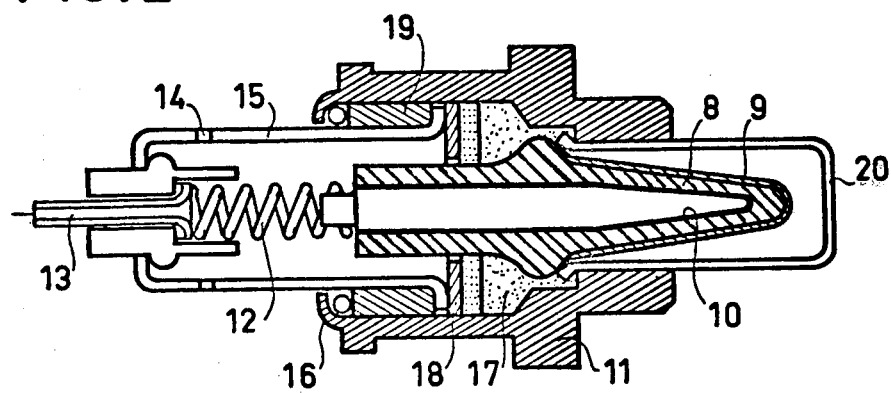
FIG. 2, a sectional view of a probe of the prior art.

FIG. 2 shows a sectional view of an analysis probe according to the prior art.

The form of the sensor more generally used in the probes of the prior art is that of an ogival-shaped tube closed at one end 8. This tube is made from zirconium oxide and it carries on its outer face a platinum layer 9 which serves as measuring electrode and on its inner face a nickel layer 10 which serves as reference electrode. One of the contacts, i.e. the contact with the external electrode 9 of the sensor, is taken directly from the body 11 which serves for securing the sensor to the outlet of the engine. The other contact, i.e. the one which is taken from the reference electrode 10, is taken by means of a spring 12 and the signal leaves by an electric wire 13.

The ogival body 8 forms a separation between a first gas volume in which the measuring electrode 9 bathes and a second gas volume in which the reference electrode 10 bathes, which is in an atmosphere of air which penetrates inside the measuring probe through apertures 14 formed in a cap 15 which closes the probe, this cap 15 being furthermore crimped at 16 so as to provide the mechanical assembly of the different parts of the probe.

One of the problems relative to the probes of the prior art resides in the sealing required between the two volumes which have just been defined, i.e. the space in which are to be found exhaust gases and the platinum electrode 9 and the space in which air and the measuring electrode 10 are to be found. This sealing is provided by a seal frequently formed from an asbestos packing impregnated with grease or talc 17, this seal being pressed against body 11 of the probe and against the body 8 of the sensor by a set of washers 18 which are themselves pressed by cap 15 which, as has already been mentioned, is crimped after assembly of the probe.

Another problem with this type of analysis probe resides in the expansion of the parts some of which are subjected to the heat of the exhaust gases whereas others are only at the ambient temperature. The expansion of the different parts is accommodated by means of a seal made from a material such as a polymer or more generally a resilient seal 19 which is mounted between body 11 of the probe and cap 15 before crimping. The precautions taken to ensure a good seal at the level of the asbestos or talc seal 17 and the precautions taken for absorbing the differences in expansion at the level of the resilient seal 19, do not prevent the body of probe 8 which is relatively massive from being subjected to thermal shocks, principally after start-up of the engine.

Furthermore, a single wire is led out from this probe, since one of the electrodes is grounded. Moreover, it is the measuring electrode which is grounded, which may present disadvantages if the ground is subject to interference or if it is necessary to supply a floating signal, for example for processing by the electronic equipment carried by a motor vehicle.

The conical part of the measuring pile 8, which projects inside the exhaust-gas manifold, is protected against these gases by a cap 20 having, depending on the embodiment, slits or holes of different forms so as to allow the exhaust gases to reach the platinum electrode 9.

Figure 3:
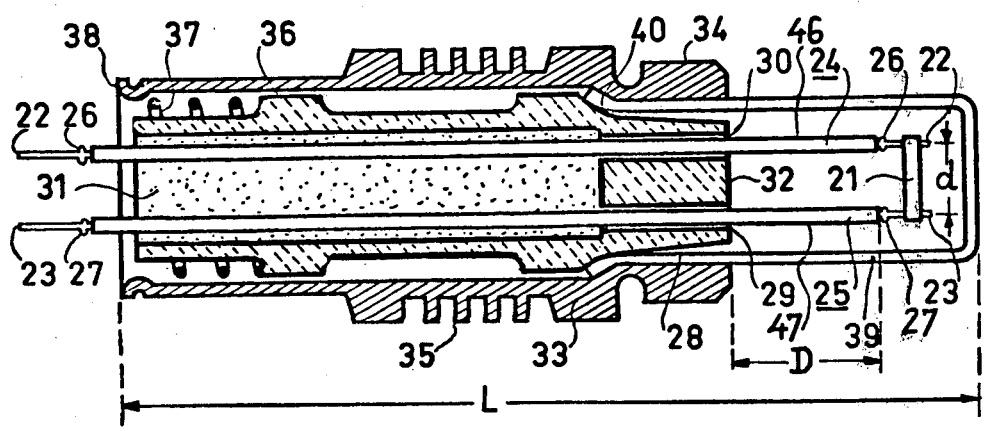
FIG. 3, a sectional view of a probe in accordance with the invention.

FIG. 3 shows a simplified sectional view of the analysis probe of the invention.

The probe of the invention uses as sensor a wafer 21 comprising a sensitive element, which operates for example according to the process described in French Pat. No. 76.13 843. This wafer delivers an electric signal between its two electrodes from which are taken connections which must resist the temperature of the exhaust gases, thermal shocks, vibrations and the corrosion of the gases. To comply with these requirements and to ensure a good electrical connection, the connections are effected by brazing two rods 22 and 23 which form both supports for the sensor and the electrical lead-outs, which brazings are made directly on the wafer of the sensor. So as to lighten the description of the probe of the invention, the details of brazing the connections to the sensor will be discussed further on.

The operation of the probe carried by wafer 21, such as described by French Pat. No. 76.13 843, requires a high impedance to be maintained between the electrical outputs of the probe so as to avoid leak currents which would cause premature aging of the active element by damage to the internal reference. To maintain a high output impedance in an exhaust-gas atmosphere which contains nonburnt hydrocarbons, which may be deposited in carbon-bearing layers which favor leak currents, is a delicate operation. It is resolved in the probe of the invention by the addition on the metal rods 22 and 23, which serve both as electric conductor and mechanical support for the sensor, of pure alumina tubes 24 and 25 having a high surface resistivity. The length of these tubes extends the leak path between the electrodes and allows impedances to be obtained greater than 1 giga-ohm at 850°.

The metal rods 22 and 23 are held in place inside the alumina tubes 24 and 25 by crushing rod 22 at 26 and rod 23 at 27, which crushing is carried out flush with the alumina tubes 24 and 25 and which prevents the rods from sliding in the tubes.

The alumina tubes 24 and 25 are themselves positioned inside the analysis probe by means of a cylindrical part 28, made from ceramic or preferably from alumina, which has two apertures 29 and 30 at one of its ends. It is through these apertures 29 and 30 that the two alumina tubes 24 and 25 pass. Securing of the alumina tubes in the cylindrical body 28 is provided by filling the inner volume, with a liquid ceramic 31, which hardens after pouring, either under the effect of the temperature, or under the effect of a chemical reaction. The advantages of filling ceramic body 28 with a liquid ceramic 31 is that the expansion coefficients are closely related if not equal, according to the nature of the ceramics, and in any case closely related to the expansion coefficient of the two alumina tubes 24 and 25.

Furthermore, the path of the leak currents between the output terminals of the sensor is formed by the fractions 46 and 47 of the two alumina tubes 24 and 25 which extend beyond the holes 29 and 30 in the ceramic body 28 as well as by the part of the surface 32 which is located between these two tubes. With body 28 made from ceramic, the surface part 32 can only improve and lengthen the path of the leak currents, better than if the assembly were assured by a metal part for example. The fractions 46 and 47 have a length D of about 2 cm whereas the surface 32 separates each of the two ceramic tubes 24 and 25 by a distance d of 5 mm. To give an order of size, the length L of the probe is approximately 10 cm. In the absence of fractions 46 and 47, the surface leak currents would then have a distance d of 5 mm to cover. The fractions 46 and 47 lengthen the path between the output terminals of the sensor 21 for the surface leak currents by 4 cm. Between the two paths of the leak currents, a ratio of 9 may be noted, i.e. a coefficient of about 10 between said paths.

Moreover, the two tubes 24 and 25 are mades from alumina of a purity between 99.5% and 99.7% by weight, so having a resistivity between $10^{11}$ Ωcm and $10^6$ Ωcm at the working temperatures of the probe. The metal rod 22 over its portion included in ceramic body 28 is then separated from metal rod 23 by ceramic tube 24, ceramic body 28 and ceramic tube 25. A current established inside body 28 between the two metal rods 22 and 23 must then pass through both alumina tubes 24 and 25.

The temperature along the gas-analysis probe decreases rapidly. For a gas temperature of 800° C. in the vicinity of sensor 21 and surface 32, the temperature is 150° C. in the vicinity of spring 37. The decrease in temperature is not uniform and is more accentuated close to surface 32. In practice, the temperature drops by 100° C. to 150° C. over a depth of about 1 cm under surface 32. The resistivity of the materials depends greatly on the temperature, the zone where the risks of electric conduction are the greatest is situated in the ceramic over a depth of about 1 cm under surface 32, air not being an electric conductor.

The distance d between the two metal tubes 22 and 23 is about equal to 5 mm. The diameter of the metal rods is 0.9 mm. The inner diameter of the ceramic tubes 24 and 25 is 1 mm and their outer diameter is 2 mm. An electric current going from rod 22 to rod 23 inside body 28 must then pass through a thickness of 1 mm due to the ceramic tubes 24 and 25 and a thickness of 5 mm due to the ceramic of body 28. The ratio between these two thicknesses is then about 5, whereas the ratio of the resistivities is greater than $10^3$. It can then be seen that only the ceramic tubes 24 and 25 are to be considered for calculating the electric resistance. Assuming that the conducting part is situated over a depth of 1 cm below surface 32, this resistance can be reckoned as being greater than 1 giga-ohm at 850° C.

Up to now, the invention has been described and is shown on FIG. 3 with two output terminals and two conductors 22 and 23. However, the field of the invention also covers the case where one or more sensors are mounted in series on the same wafer 21, or else the case where one or more additional electrodes are used. In this case, the probe of the invention comprises more than two rods 22 and 23 and more than two alumina tubes 24 and 25, the number of outputs depending on the measurements effected either at the level of sensor 21, or at the level of the processing electronics, but in all cases the ground of the measuring circuit is different from the ground of the engine on which the probe is mounted.

The ceramic body 28 is itself mounted, from the mechanical point of view, in a metal body 33 which comprises a thread 34 for screwing the probe into a threaded portion provided on the silencer of the engine to be checked. But, this metal body 33 further comprises a series of fins 35 for removing the heat picked up on the exhaust-gas manifold side. This results mainly in avoiding overheating of the cable through which the electric signals leave and of the mechanical part of the probe, which could damage them.

Furthermore, metal body 28 comprises at its end opposite that which carries the sensor a shoulder 36 against which bears a spring 37 which is held after assembly of the probe by the end 38 of the metal casing 33. Thus, spring 37 absorbs the expansions of the different parts and avoids breakages under the stress of different expansion coefficients between the internal ceramic body 28 and the external metal casing 33. It has no electrical connection function.

The probe is finally finished by a cap 39, which will be described further on, this cap being held in place at 40 between a shoulder in the internal ceramic body 28 and the external metal casing 33.

The fact of using as sensor a sensor with internal reference overcomes the sealing problem which was discussed in connection with the probes of the prior art. Thus, in the probe of the invention, it is no longer necessary to have a good seal formed by a graphite-impregnated asbestos or talc seal and cap 39 may present a few gas leaks at shoulder 40 without that having any consequence on the accuracy of the measurements effected.

FIG. 1 shows a sectional and schematical view of the sensor used in this type of probe. It was mentioned that the connections are taken from the sensor by means of brazing. FIGS. 4 and 5 take up again in detail the method of securing rods 22 and 23 by brazing to the wafer of the sensor.

Figure 4:
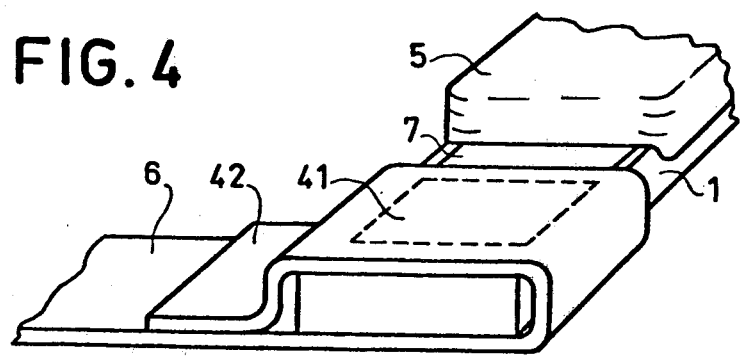
FIG. 4, a detail view showing a first type of electrical contact take-off on the sensor.

FIG. 4 shows a first type of brazing by means of metal strips.

FIG. 4 shows the end of a sensor of which there can be seen the substrate 1 and the enamel layer 5 which covers the concentration pile properly speaking. On the end considered of the substrate there is deposited a brazing filler-metal layer 7. The brazing filler-metal layer must have a melting point greater than that of the maximum temperature of the gases, i.e. about 900° C. It may be in the form of a strip which is inserted between wafer 1 and the connection to be welded, or by electrochemical deposits, or by silk-screened deposits, or by several of these processes at one and the same time. The brazing filler-metal is provided either on the end of the connection which is to be brazed to the wafer, or on the wafer, or on both at the same time. This filler-metal may be for example gold whose melting temperature is 1063° C., or a gold alloy such for example as gold-nickel with 15% nickel whose melting temperature is 950° C.

The connecting strip 6 forms a loop about the end of wafer 1 and is welded by thermocompression in the zone shown by a broken line 41. It is advantageous, because of the vibrations inevitable to the operation of a thermal engine, for this first brazing by thermocompression to be completed by a second electric welding of the strip on itself in the region 42. Such a connection is effected at both ends of the wafer since an electric connection is required from each of the electrodes of the concentration pile.

Figure 5:
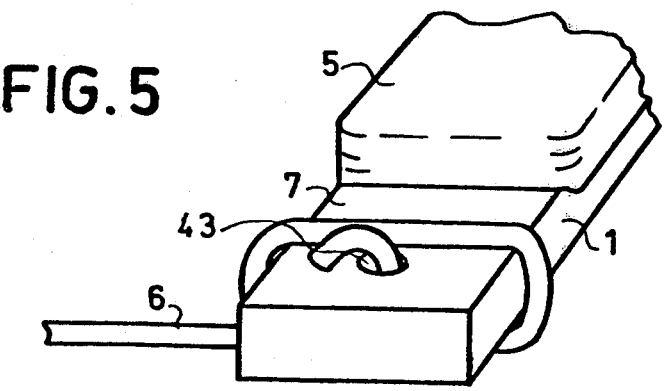
FIG. 5, a detail view showing a second type of electrical contact take-off on the sensor.

FIG. 5 shows a variation of FIG. 4 in which the connections are formed not by means of metal strips but by means of a wire. In this second case, the brazing itself is effected as has just been discussed in connection with FIG. 4, but instead of welding the connecting wire 6 back on itself as was the case for the connecting strip by means of an electric weld 42, the connecting wire 6 forms a complete loop around the wafer 1 of the sensor then passes through a hole 43 made in this wafer and is there fixed by brazing. This ensures that the brazing will not break following vibrations of the running engine.

Figure 6:
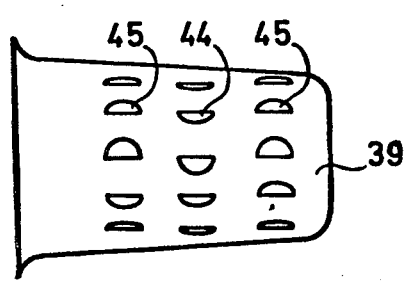
FIG. 6, a view of the protection cap of the probe.

FIG. 6 shows the cap 39 which completes the probe of the invention and protects the sensor 21. This cap is a metal body cylindrical in shape or in the shape of a truncated cone with a round section. It comprises, at its open end, a shoulder 40 which enables the cap to be locked between two corresponding shoulders on the metal casing 33 and the ceramic body 28. So as to allow the gases to reach the sensor, the sensor has passing through its curved wall holes 44 and 45, placed head-to-tail in alternating series, semicircular in shape and obtained by milling the cap along a milling axis orthogonal to the axis of symmetry of the cap.

The invention has been described with respect to the example of a sensor detecting a partial pressure or oxygen concentration in the exhaust gases of an internal combustion engine but it also applies to all types of probes using a sensor formed on a wafer in accordance with thin-layer technology. This type of probe is suitable for measurements such as qualitative or quantitative measurements in industrial gases for example.

Similarly, the invention covers probes in which a number of connections greater than the two connections which have been shown in the figures might be used such for example as probes comprising a heating member with its connection or probes comprising a measuring sensor and an alarm or regulation sensor.

For all these types of measuring probes, the connection taken from the metal rods which extend from the body at its end opposite that which carries the sensor properly speaking is made either directly by welding, or by a connector, but all have the particularity of having an electrical ground which is isolated.

What is claimed is:

1. A gas-analysis probe comprising:
   a gas sensor having two contact electrodes and an inner reference electrode for being entirely immersed in the gases to be analyzed;
   a metal casing having an external side and an internal side and being provided with cooling fins on the external side and with a first shoulder at one end of the internal side and with a recess extending from said one end thereof toward the other end;
   a hollow ceramic body within said metal casing, and having an external side and an internal side and a second shoulder on said external side, and at least two apertures at one end of said hollow ceramic body;
   a spring bearing on said first and second shoulders and pushing said hollow ceramic body toward said other end of said casing;
   at least two metal rods each brazed at one of their ends to one of said contact electrodes of said gas sensor for conducting the electric signal thereof and sheathed by two high-resistivity ceramic tubes in which they are secured, said ceramic tubes having the same diameter as the apertures so as to allow the positioning of said metal rods in said apertures;

a filling formed by hardenable liquid ceramic, for filling said recess of said ceramic body so as to secure said metal rods against movement, said metal rods being so positioned so that they extend beyond a second end of the hollow ceramic body.

2. A gas-analysis probe as in claim 1, wherein the composition of said ceramic tubes contains more than 99.5% by weight of alumina.

3. A gas-analysis probe as in claim 1, wherein a fraction of said ceramic tubes extend beyond the apertures of said ceramic body.

4. A gas-analysis probe as claimed in one of claims 1 to 3, wherein each connection on the electrodes of the sensor is formed by brazing a metal rod on one end of the wafer of the sensor by means of at least one solid layer of filler-metal for brazing, previously deposited between rod and wafer, this filler-metal having a melting temperature greater than 900° C., the brazing on thin layers being effected by thermocompression of the region in which the filler-metal layer is inserted between the rod and the wafer.

5. A gas-analysis probe as claimed in claim 4, wherein said solid layer of filler-metal for brazing is deposited by silk-screen printing on the wafer.

6. A gas-analysis probe as claimed in claim 4, wherein said solid layer of filler-metal for brazing is deposited by electro-chemistry on said metal rod.

7. A gas-analysis probe as claimed in claim 4, wherein each metal connecting rod is looped back once around the wafer and welded to itself.

8. A gas-analysis probe as claimed in claim 4, wherein each metal connecting rod is looped back at least once around the wafer and brazed in a hole formed in said wafer.

9. A gas-analysis probe as claimed in one of claims 1 to 3, wherein each metal connecting rod is looped back at least once around the wafer and brazed in a hole formed in said wafer.

10. A gas-analysis probe as claimed in one of claims 1 to 3, wherein said sensor is protected by a metal cap fixed between said metal casing and said ceramic body by means of a solder, which cap has semicircular holes pierced in its curved wall, in alternating series, formed by milling said cap along an axis orthogonal to the axis of the cap.

* * * * *